United States Patent [19]
Condon et al.

[11] Patent Number: 5,159,920
[45] Date of Patent: Nov. 3, 1992

[54] SCOPE AND STENT SYSTEM

[75] Inventors: Dennis E. Condon, Santa Barbara; Robert S. Bley, Goleta; Bobby Purkait, Santa Barbara, all of Calif.

[73] Assignee: Mentor Corporation, Goleta, Calif.

[21] Appl. No.: 539,865

[22] Filed: Jun. 18, 1990

[51] Int. Cl.$^5$ ............................................. A61B 17/00
[52] U.S. Cl. ........................................ 128/6; 606/108; 128/662.06; 128/4
[58] Field of Search ..................... 606/108; 128/4-6, 128/663.01, 662.06; 604/8-11

[56] References Cited

U.S. PATENT DOCUMENTS

| | | | |
|---|---|---|---|
| 4,782,819 | 11/1988 | Adair | 128/6 |
| 4,834,068 | 5/1989 | Gottesman | 128/4 |
| 4,913,683 | 4/1990 | Gregory | 604/8 |
| 4,990,151 | 2/1991 | Wallsten | 606/108 |
| 4,991,565 | 2/1991 | Takahashi et al. | 128/4 |
| 4,994,066 | 2/1991 | Voss | 606/108 |
| 4,998,527 | 3/1991 | Meyer | 128/6 |
| 5,022,349 | 6/1991 | Biegeleisen | 128/662.06 |
| 5,024,234 | 6/1991 | Leary et al. | 128/663.01 |

*Primary Examiner*—Robert A. Hafer
*Assistant Examiner*—Kerry Owens
*Attorney, Agent, or Firm*—Blakely, Sokoloff, Taylor & Zafman

[57] ABSTRACT

A scope and stent system, the scope providing visibility not only through the urethra but also through the ureter during the insertion and placement of a ureteral stent. The scope is in the form of a fiber optic bundle having an appropriate provision for lighting and lensing thereof, and preferably having a video camera and monitor responsive to the image formed at the opposite end of the scope for viewing during the scope insertion process. The fiber optic bundle itself is made sufficiently small so that the entire scope may be fabricated with the appropriate dimensions of a typical stent guide wire and made sufficiently flexible for negotiating a tortuous path as required. The scope may be first inserted through an open-ended stent and through the urethra, the bladder and the ureter, and then the stent inserted thereover through the use of an appropriate stent pusher, or alternatively the scope, stent and stent pusher may be advanced together, the scope allowing observation of the procedure and the nature and extent of any obstructions encountered in the insertion process. Alternate embodiments include the provision of an additional working channel within the stent to allow an additional instrument such as a laser lithotriptor to be utilized in conjunction with the placement of the stent, as well as alternate forms of scope systems.

33 Claims, 5 Drawing Sheets

SCOPE AND STENT SYSTEM

BACKGROUND OF THE INVENTION

1. Field of the Invention

The present invention relates to the field of Urology.

2. Prior Art

Ureteral stents to provide drainage from the kidneys to the bladder are placed in position in the ureter through an appropriate scope system, typically in retrograde fashion through a cystoscope having a working channel large enough to put the required instruments through, such as stents, guide wires, forceps and the like. Placement of such a large scope into a patient's urethra requires anesthesia and a "cysto-room" environment.

After the scope is placed through the urethra and the tip is within the bladder, the stent is then advanced through the scope, through the bladder and into the ureter. At the point where the stent or part of the stent is in the ureter, the tip of the stent and its full location is no longer visible directly by means of the scope, the scope being too large to itself also be advanced into the ureter. Thus the stent and guide wire must be positioned and progress must be viewed by means of fluoroscopy or ultrasound from outside the patient. Manipulation of the stent and cystoscope while trying to interpret the image given by either fluoroscopy or ultrasound can become quite difficult. In any event, after the stent is in the desired location as detected by a combination of direct vision and fluoroscopy or ultrasound, the stent is left in place by some means of pushing the stent off of its working guide wire or stylet, after which the guide wire or stylet is removed, followed by the removal of the scope from the urethra.

This procedure, though quite routine, is quite cumbersome, as the doctor operating the cystoscope must be sitting low between the patient's legs, and must bend over to view through the cystoscope. Since direct vision is lost anywhere past the bladder, it is not possible for the doctor to actually see where the stent is going, what the condition of the ureter is, what potential obstructions look like, or if a kidney stone is embedded within the walls of the ureter. Thus upon encountering an obstruction, the doctor's options are highly limited, the most obvious option merely being to try to negotiate past the obstruction and proceed with the placement of the stent irrespective of the nature of the obstruction, presence of a kidney stone, etc. For this purpose various forms of stents and guide wires are known.

One form of stent and guide wire system is shown in U.S. Pat. No. 4,307,723. As shown therein, the stent is an elongated, flexible, generally cylindrical member having the proximal end of the stent closed and set in the form of a hook, with the other end also set in the form of a hook with a longitudinal intermediate portion connecting the hooked ends. A stylet is inserted through the open end of the stent and passed through substantially the full length of the stent to straighten both hooks. Also, a stent pusher is threaded over the wire stylet and inserted into the open end of the stent a certain amount to allow the partial withdrawal and redirection of the stent if necessary during the retrograde cystoscope insertion process hereinbefore described. Once the stent is properly positioned, the stylet and stent pusher are removed by withdrawing the stent pusher while holding the wire stylet, causing the stent and stent pusher to disengage, after which the wire stylet and then the stent pusher are withdrawn.

Other stents are of somewhat similar construction to the foregoing though open at the proximal end, with a stent pusher being used to push against the distal end of the stent to encourage the same to move together with (or after) the guide wire into position, after which the stent pusher is used to retain the stent in position as the guide wire is withdrawn, with the stent pusher itself then being withdrawn.

In U.S. Pat. No. 4,610,657, a ureteral stent is disclosed having both ends thereof open, but with the opening at the proximal end being smaller than the opening of the lumen and distal end. In this way, a small guide wire may be inserted through the lumen and through the proximal end to negotiate past obstructions, etc., or alternatively a larger guide wire could be inserted to pass through the lumen, but not through the smaller opening in the proximal end, to act as a stent pusher for stent insertion purposes.

In addition to the foregoing, two-piece guide wires are also known. Such guide wires generally comprise a helically wound flexible outer guide wire portion typically closed at the proximal end, and a solid, more rigid inner guide wire removably positioned within the flexible outer guide wire portion. In this manner, the two guide wire members together may be used as a single guide wire and if necessary, the more rigid central guide wire may be partially withdrawn, making the proximal end of the outer guide wire member more flexible to better manipulate the same past obstructions (See, for instance, U.S. Pat. No. 4,713,049 for a dual guide wire system of this general type).

Obviously, from the foregoing description, cystoscopes for passing through the urethra and into the bladder and having an auxiliary port for insertion of the stent, guide wire, pusher, etc. are well known. In general the auxiliary port of such devices is located to the side of the fiber optic scope, which scope is normally as large as or larger than the stent itself. Thus the overall combination of the fiber optic bundle, cystoscope body, stent, stent pusher, guide wire, etc. is relatively large, requiring that the patient be anesthetized as mentioned before, and being much too large for passage beyond the bladder into the ureter. See for instance, U.S. Pat. No. 4,738,659 disclosing a catheter for use with a cystoscopic lens. Also, of course, such fiber optic scopes are themselves well known in the prior art, such as by way of example as disclosed in U.S. Pat. No. 3,417,745.

SUMMARY OF THE INVENTION

A scope and stent system, the scope providing visibility not only through the urethra but also through the ureter during the insertion and placement of a ureteral stent. The scope is in the form of a fiber optic bundle having an appropriate provision for lighting and lensing thereof, and preferably having a video camera and monitor responsive to the image formed at the opposite end of the scope for viewing during the scope insertion process. The fiber optic bundle itself is made sufficiently small so that the entire scope may be fabricated with the approximate dimensions of a typical stent guide wire and made sufficiently flexible for negotiating a tortuous path as required. The scope may be first inserted through an open-ended stent and through the urethra, the bladder and the ureter, and then the stent inserted thereover through the use of an appropriate stent pusher, or alternatively the scope, stent and stent pusher may be advanced together, the scope allowing observation of the procedure and the nature and extent of any obstructions encountered in the insertion process. Alternate embodiments include the provision of an additional working channel within the stent to allow an additional instrument such as a laser lithotriptor to be utilized in conjunction with the placement of the stent, as well as alternate forms of scope systems.

DETAILED DESCRIPTION OF THE INVENTION

Figure 1:
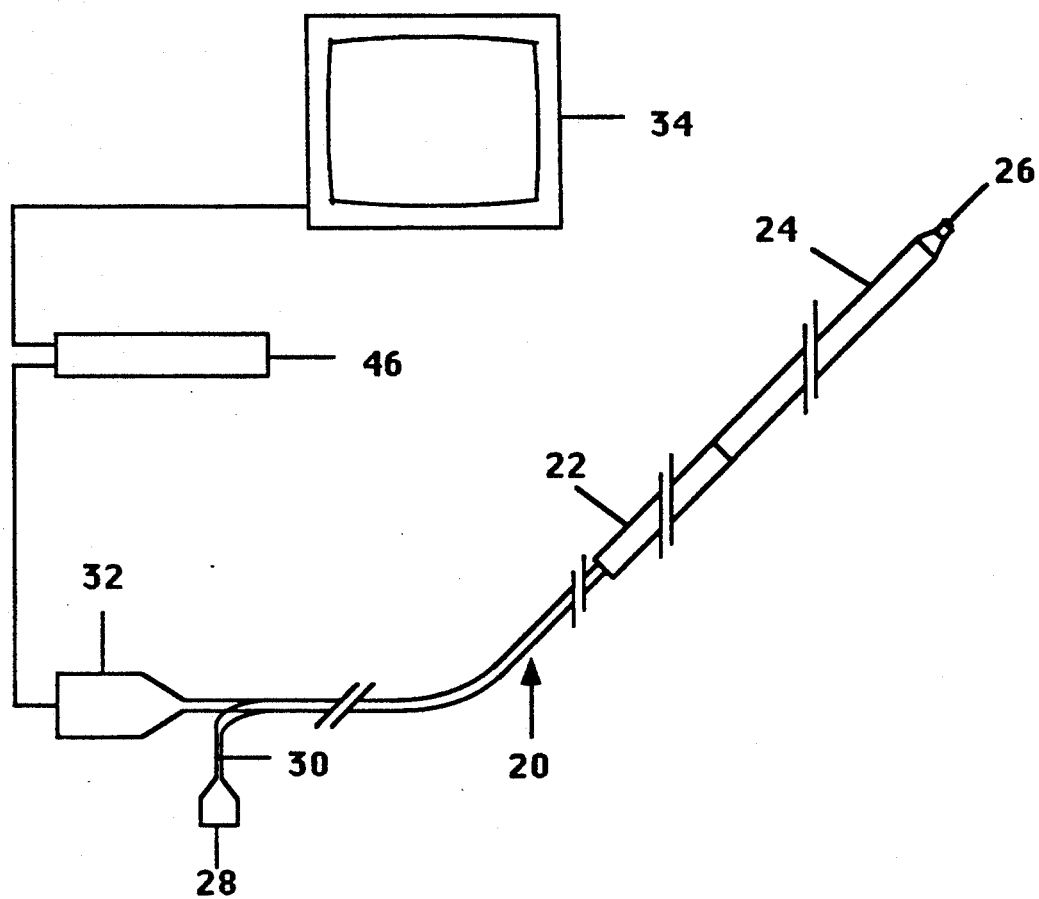
FIG. 1 is a schematic diagram, not to scale, illustrating the system of one embodiment of the present invention.

First referring to FIG. 1, a schematic diagram (not to scale) of a typical system in accordance with one embodiment of the present invention may be seen. As shown therein, a long, small-diameter fiber optic scope, generally indicated by the numeral 20, extends upward through a stent pusher 22 and open ended stent 24 with the proximal end 26 thereof extending through the open proximal end of the stent. Adjacent the opposite end of the scope 20 is a light source 28 feeding a fraction of the optical fibers 30 with sufficient light to adequately illuminate the region surrounding the proximal end 26 of the scope so that an image of adequate intensity and contrast may be received at the proximal end of the fiber optic image bundle. Also at the end of the scope 20 adjacent to light source 28 is a video camera 32 with appropriate lensing to convert the image at the associated end of the fiber optic bundle to a video signal for display on video monitor 34.

With the system shown in FIG. 1, the urologist may insert the scope 20 through the urethra, the bladder and the ureter, being able to constantly monitor the region of all three adjacent tip 26 of the scope to generally observe the condition thereof and to observe any stone or other obstruction. This may be done while advancing the stent 24 and pusher 22 simultaneously therewith, or alternatively prior to advancing the stent and stent pusher thereover so that the same will follow the pre-inserted scope. Similarly of course, the stent and pusher may be advanced with the scope until such time as an obstruction is encountered, and then the scope advanced and manipulated as required to advance past the obstruction, the stent pusher then being advanced to advance the stent past the obstruction also. In this manner not only is the urethra observed, as it is with prior art cystoscopes, but in addition the entire ureter may also be observed, including the nature and extent of obstructions, stones and any other unusual condition which may be encountered. As such, the urologist will have far better knowledge of the patient's condition and a far better control over the insertion process than is now possible. Of course once the stent is placed in position, the scope 20 is first removed from the stent while the stent is held in position by the pusher, with the stent and pusher thereafter being removed from the urethra either separately or together as desired.

Figure 2:
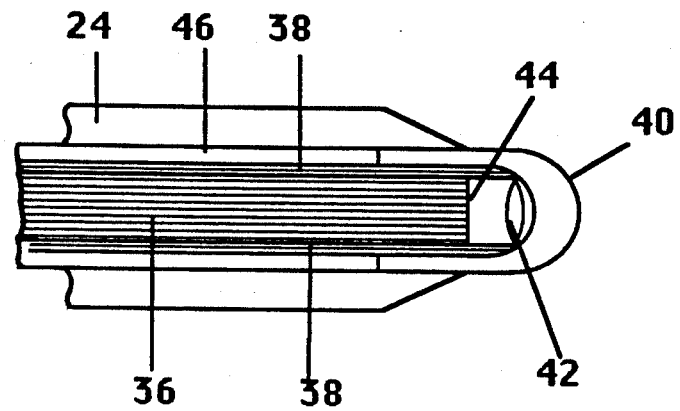
FIG. 2 is a diagram illustrating schematically the tip of the scope and stent of FIG. 1.

The scope and particularly the proximal end thereof may take various forms. By way of example, one relatively simple form for the proximal end 26 of the scope is schematically illustrated in FIG. 2. Here the fiber optic bundle is shown as two portions, mainly a central portion 36 carrying the image focused onto the proximal end thereof to the opposite end of the bundle for pickup by the video camera 32, and a circumferential portion 38 for carrying light from the light source 28 (See FIG. 1) through the dome-shaped transparent cap 40 to illuminate the surrounding tissue. The image of the illuminated tissue is focused by a lens 42 onto the end 44 of the central portion 36 of the fiber optic bundle, the design and optical characteristics of the cap 40 also being important in the imaging system. In general the tip of the fiber optic bundle, cap 40, lens 42 etc. will be a rigid assembly, though the remainder of the fiber optic bundle down to a position adjacent the opposite end thereof will in general be left flexible, the same in general being covered with a flexible sheath 46 extending from cap 40 over most of the remaining scope length. Finally, also shown in FIG. 2 is the proximal end of the stent 24, the same typically being tapered as shown to help in opening an obstruction for the passage of the stent therethrough.

The light source 28 (See FIG. 1) may be a conventional light source for such purposes and for that matter, the size of the fiber optic elements used for carrying the light to the distal end 26 of the scope 20 may be larger than the fiber optic elements in the central section 36 (See FIG. 2) of the scope as the fiber optic elements in the central section 36 should be as small as reasonably practical to provide good resolution in the image picked up by the video camera 32 and displayed on the video monitor 34. In that regard, with respect to lighting, solid state video cameras have excellent sensitivity, and if necessary, image repetition rates may be purposely reduced to increase the sensitivity of the camera as obstructions, when encountered, normally will be viewed in a still or near still condition. Also regarding resolution, as stated before, small diameter fiber optic elements should be used to provide good resolution in the resulting image, though it should be noted that because the present invention provides a direct vision capability in a medical procedure wherein no similar direct vision capability was available in the prior art, an image of somewhat limited resolution is still highly useful for the intended purpose (if desired, computer enhancement of the video image could be incorporated). Finally, for training purposes, insurance records, malpractice defense or merely later reference, a video recorder 46 may be used to video tape the entire procedure.

Figure 3:
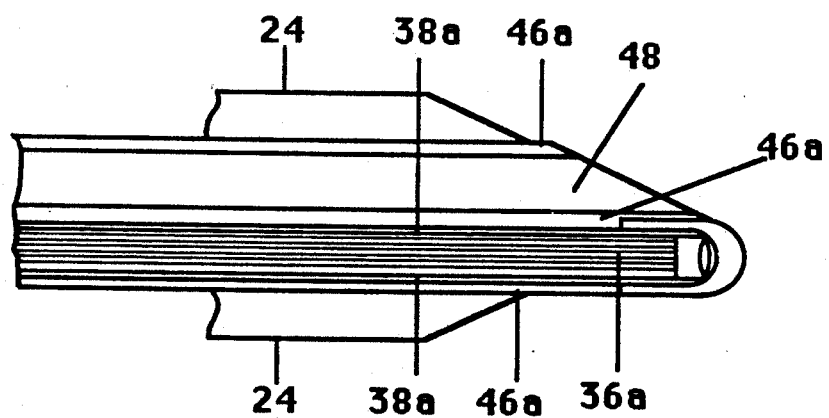
FIG. 3 is a diagram similar to FIG. 2, though illustrating an alternate embodiment scope having an auxiliary port therein.
Figure 4:
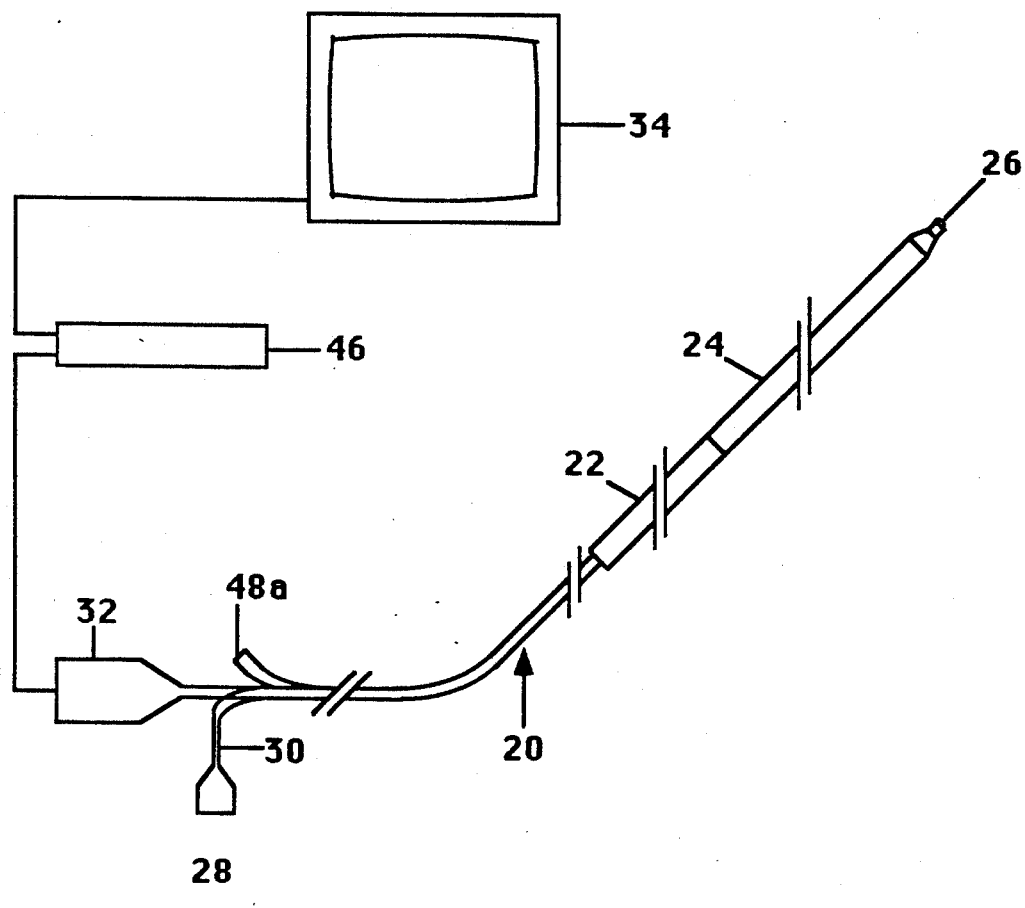
FIG. 4 is a schematic diagram similar to FIG. 1 though illustrating schematically the access port 48a for the auxiliary port of the scope.

Now referring to FIG. 3, an alternate embodiment may be seen. In this embodiment, the scope is generally the same design as that illustrated in FIG. 2, though it is fabricated in an even smaller form and located off axis, with the flexible sheathing 46a being larger and having an auxiliary passage 48 therein for irrigation purposes, for lithotripsy purposes, for injection of a radiopaque material, etc. This auxiliary opening may be smaller than, approximately equal to or even larger than the scope as desired. Of course, the outer diameter of the flexible sheath 46a would be sized to be compatible with standard open-ended stents 24 so as to serve as the guide wire therefore as hereinbefore described. In that regard, assuming the assembly is sufficiently flexible, opening 48 might also be used to receive a guide wire to temporarily stiffen the assembly as may be required from time to time, much like two-piece guide wire assemblies of the prior art. The opposite end 48a of the port is accessible from adjacent the opposite end of the scope, as shown schematically in FIG. 4.

In the embodiment of FIG. 3, the scope is in effect displaced off axis and accordingly may image part of the ureter circumference better than other parts. On the other hand, the scope may be manipulated in rotation to better view anything desired to be viewed by the urologist. Further, the non-symmetrical tip of FIG. 3 may assist in negotiating past obstructions by allowing the manipulation of the scope tip to the best region for encouraging the obstruction open and the passage of the assembly therethrough. For this purpose, the camera 32 and light source 28 (See FIG. 1) may be rotated with the scope, though it is more convenient to mount the scope with respect to the lensing system for the camera 32 on a rotary support so that the image plane of the fiber optic bundle as viewed by the camera is rotatable with respect to the camera while being maintained at the proper axial position with respect to the lensing system. Further, the light system 28 and the length of the fiber optic bundle extending thereto may be proportioned and positioned so that a number of full turns of the scope may be made without moving the light system 28 by merely winding the lighting fiber optic bundle portion around the viewing fiber optic bundle portion as the scope is rotated, or alternatively, a rotatable light system may be used.

Figure 5:
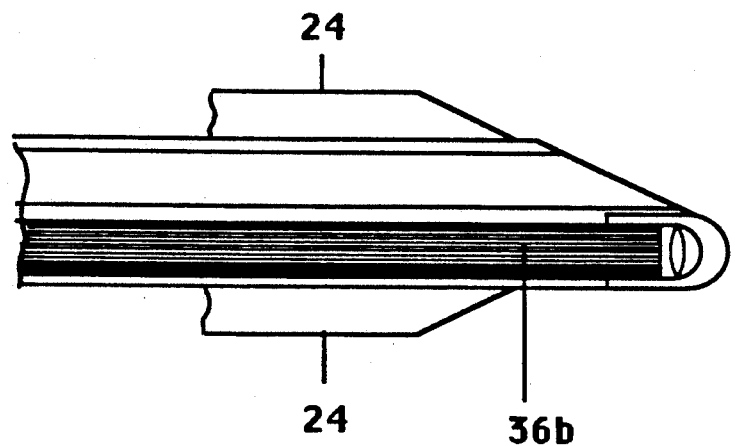
FIG. 5 is a diagram similar to FIG. 3 though illustrating a further alternate embodiment of scope structure.
Figure 6:
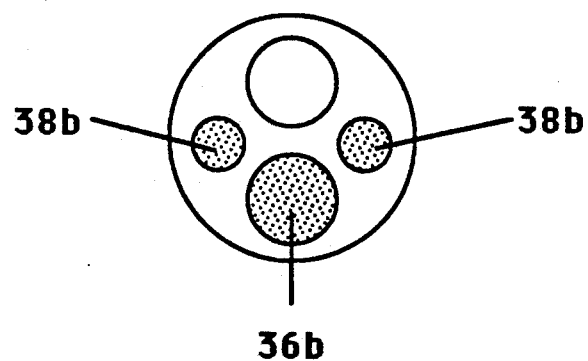
FIG. 6 is a typical cross section of the embodiment of FIG. 5.

In the embodiments illustrated in FIGS. 2 and 3, the lighting portion of the fiber optic bundle is shown as being concentric with the image portion of the fiber optic bundle. This of course is by no means a limitation of the present invention. By way of specific example, FIG. 5 illustrates an embodiment similar in many respects to that of FIG. 3, though here the image fiber optic bundle 36b is larger than the fiber optic bundle 36a of the embodiment of FIG. 3. As may be seen in the cross section of FIG. 6, separate lighting fiber optic bundles 38b are disposed slightly above and to each side of the image bundle 36b. Such an arrangement has certain physical advantages in that it provides for better utilization of the limited cross sectional area available for the scope, and has optical advantages in that the same will more easily minimize the direct reflection of the light back to the image plane at the proximal end of the scope, which direct reflection will tend to reduce the image contrast obtained and wash out the image presented on the video monitor.

Figure 7:
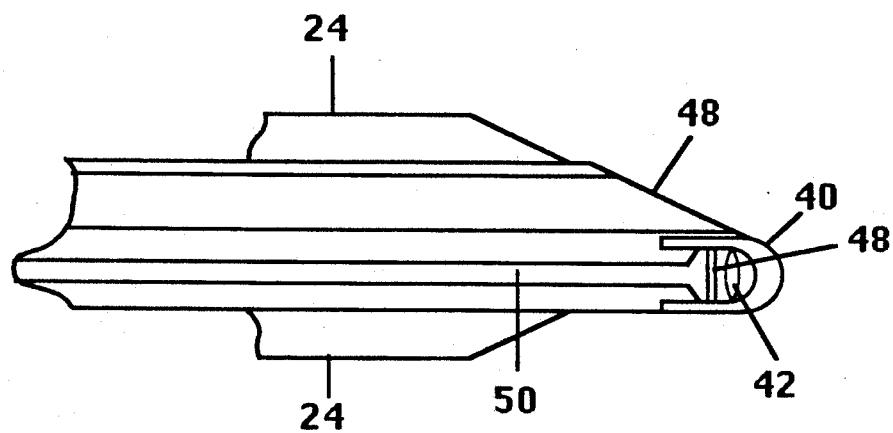
FIG. 7 is a schematic diagram illustrating a still further embodiment of scope structure.

In the embodiments of the invention hereinbefore described, the fiber optic bundle is used to convey an image on an image plane adjacent the proximal end of the scope to the opposite end of the scope for pickup by an appropriately lensed video camera. It is possible, however, to provide a video sensor array small enough and with adequate resolution to be useful in the proximal end of the scope. Thus as shown schematically in FIG. 7 a video sensor array 48 is placed at the image plane at the proximal end of the scope, which sensor array is coupled with the remainder of the video camera electronics through a cable 50 attached thereto. In that regard, the overall system of such embodiment generally appears as shown in FIG. 1, camera 32 as described with respect to the prior embodiments of the invention now comprising the camera electronics, timing circuits, etc., but with the sensor array itself being removed therefrom and connected by way of cable 50 as hereinbefore described. In such an arrangement, reduced resolution and perhaps reduced frame rates may have to be used, using current technology, though the camera electronics could easily include a frame buffer so that the resulting image could be displayed on a conventional video monitor, recorded on a conventional VCR, etc.

Figure 8:
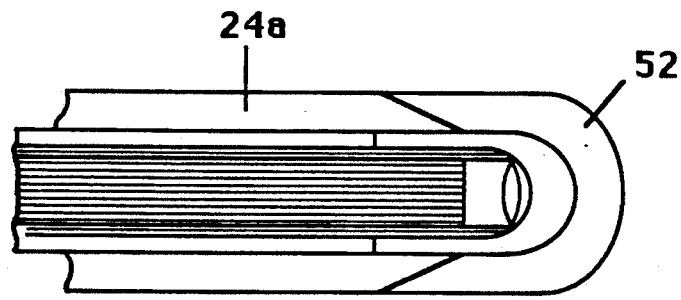
FIG. 8 is a schematic diagram similar to FIG. 2 though illustrating the use of the scope thereof with a closed transparent end stent.

Now referring to FIG. 8, a still further embodiment of the invention may be seen. In this embodiment, the scope and system associated therewith may be identical to that described with respect to FIGS. 1 and 2. The stent 24 however, rather than being open-ended as shown in FIG. 2, may be provided with an integrally molded closed transparent end 52 which not only allows the scope itself to act as a stent pusher, but which also allows the scope to view directly through the stent itself.

There has been disclosed and described herein new and unique scope and stent systems which will provide a viewing capability during insertion of the stent. The resulting smaller overall system will alleviate the need for anesthesia and eliminate the post-procedure discomfort usually involved with the use of a cystoscope. Since no anesthesia would be required, the overall cost to the patient and to the insurance companies would be greatly reduced, at the same time eliminating the exposure to x-rays by both the physician and the patient. The procedure can now be done in an office setting rather than a hospital cysto-room, making it more convenient and cheaper for all involved.

The additional working channel in the embodiments of FIGS. 3 through 7 could be used not only in conjunction with a laser lithotriptor allowing a stone to be blasted and then the stent left in place without any reinsertion of instruments, but also be used for the infusion of radiopaque liquids in case radiographic visualization of the entire system was needed. Also in the event a kidney stone is encountered, if the same is mobile it is sometimes possible to push the stone into the kidney where it is then possible to blast it with an ESWL machine. The present invention allows the stone to be pushed into the kidney under direct vision.

Thus as can be seen from the foregoing disclosure, the stent is the largest part of the scope system, which allows direct visual access of the entire pathway. Obviously, the scope is also usable without a stent. Accordingly, the present invention may be used in all procedures in the ureter that require visualization and/or a stent in all office ureteral diagnostic procedures, all ureteral stone lithotripsy procedures and all ureteral stent procedures. Thus while the present invention has been disclosed and described herein with respect to certain preferred embodiments thereof, it will be understood by those skilled in the art that various changes in form and detail may be made therein without departing from the spirit and scope thereof.

We claim:

1. A scope and stent comprising:

a ureteral stent in the form of a relatively flexible tubular member having first and second stent ends;

an elongate flexible scope means having a first scope end for insertion into a patient's urinary tract and a second scope end for remaining outside a patient's body, said scope means having:

illumination means for illuminating objects in the vicinity of said first scope end;

imaging means adjacent said first end thereof for providing an image of objects in the vicinity of said first end of said scope means;

conveying means for conveying the image provided by said imaging means to the second end of said scope for viewing when said scope is inserted into a patient's urinary tract;

said scope means being disposed within the lumen of said stent and supporting said stent along a longitudinal axis of said stent against buckling of said stent during insertion of said stent into the urinary tract, including the ureter, such that said stent is always locally essentially parallel with said scope means as said stent is inserted into the urinary tract, whereby said scope means may provide a viewing capability for the stent insertion procedure within the urinary tract, including the ureter.

2. The scope and stent of claim 1 wherein said illumination means comprises a source of illumination adjacent said second end of said scope means and a fiber optic bundle extending therefrom through said scope means to said first end thereof for illuminating objects in the vicinity of said first scope end.

3. The scope and stent of claim 1 wherein said conveying means comprises a fiber optic bundle having first and second ends adjacent said first and second ends of said scope means, respectively, said imaging means comprising a lens means for providing an image on said first end of said fiber optic bundle.

4. The scope and stent of claim 3 further comprising a video camera and a video monitor, said video camera being disposed and lensed to receive an image formed at said second end of said fiber optic bundle and to convert the same to a video signal, said video monitor being coupled to said video camera to display an image responsive to said video signal.

5. The scope and stent of claim 4 further comprising a video recorder coupled to said video camera for recording said video signal.

6. The scope and stent of claim 1 wherein said stent is open at said first end thereof, whereby the stent and scope may be inserted together using a stent pusher and the scope may be advanced beyond the stent as desired.

7. The scope and stent of claim 1 wherein said first end of said stent is transparent and closed, whereby the scope may be used as a stent pusher during insertion thereof.

8. The scope and stent of claim 1 wherein said scope includes an auxiliary opening extending from adjacent said first end thereof along at least most of the length of said scope.

9. The scope and stent of claim 8 wherein said auxiliary opening is an opening sized to receive a laser lithotriptor.

10. The scope and stent of claim 1 wherein said conveying means comprises a video sensor adjacent said first end of said scope and electrically coupled through said scope means to video camera electronics means adjacent said second end of said scope, and further comprising a video monitor coupled to said video camera electronics to display an image responsive to the image received by said video sensor, said imaging means being a lens means for providing an image on said video sensor.

11. A scope comprising;

an elongate flexible scope means having a first scope end for insertion into a patient's urinary tract and a second scope end for remaining outside a patient's body, said scope means having:

illumination means for illuminating objects in the vicinity of said first scope end;

imaging means adjacent said first end thereof for providing an image of objects in the vicinity of said first end of said scope means;

conveying means for conveying the image provided by said imaging means to the second end of said scope for viewing when said scope is inserted into a patient's urinary tract;

said scope means being disposed within the lumen of a ureteral stent and supporting said stent along a longitudinal axis of said stent against buckling of said stent during insertion of said stent into the urinary tract, including the ureter, such that said stent is always locally essentially parallel with said scope means as said stent is inserted into the urinary tract to traverse a patient's urethra, bladder and ureter, whereby said scope means may be used for examination purposes and may provide a viewing capability for medical procedures such as stent insertion throughout the length of the urinary tract, including the ureter.

12. The scope of claim 11 wherein said illumination means comprises a source of illumination adjacent said second end of said scope means and a fiber optic bundle extending therefrom through said scope means to said first end thereof for illuminating objects in the vicinity of said first scope end.

13. The scope of claim 11 wherein said conveying means comprises a fiber optic bundle having first and second ends adjacent said first and second ends of said scope means, respectively, said imaging means comprising a lens means for providing an image on said first end of said fiber optic bundle.

14. The scope of claim 13 further comprising a video camera and a video monitor, said video camera being disposed and lensed to receive an image formed at said second end of said fiber optic bundle and to convert the same to a video signal, said video monitor being coupled to said video camera to display an image responsive to said video signal.

15. The scope of claim 14 further comprising a video recorder coupled to said video camera for recording said video signal.

16. The scope of claim 11 wherein said said scope is of sufficient length so that said scope may be inserted together with a stent or the scope may be first inserted and a stent then inserted over said scope by a stent pusher also disposed over said scope.

17. The scope of claim 11 wherein said scope may be used as a stent pusher during insertion of a closed proximal end stent.

18. The scope of claim 11 wherein said scope includes an auxiliary opening extending from adjacent said first end thereof along at least most of the length of said scope.

19. The scope of claim 18 wherein said auxiliary opening is an opening sized to receive of a laser lithotriptor.

20. The scope of claim 11 wherein said conveying means comprises a video sensor adjacent said first end of said scope and electrically coupled through said scope means to video camera electronics means adjacent said second end of said scope, and further comprising a video monitor coupled to said video camera electronics to display an image responsive to the image received by said video sensor, said imaging means being a lens means for providing an image on said video sensor.

21. The scope of claim 11 wherein said scope has a stiffness so as to be capable of serving as a guide wire for the insertion of a ureteral stent.

22. A method of inserting a stent comprising:
(a) providing a ureteral stent in the form of a relatively flexible hollow tubular member having first and second ends;
(b) providing an elongate flexible scope means having a first scope end for insertion into a patient's urinary tract and a second scope end for remaining outside a patient's body, said scope means having;
illumination means for providing illumination through said first end thereof;
imaging means in said scope means adjacent said first end thereof for providing an image of objects in the vicinity of said first end of said scope means;
conveying means for conveying the image provided by said imaging means to the second end of said scope for viewing when said scope is inserted into a patient's urinary tract;
said scope means being disposed within the lumen of said stent and supporting said stent along a longitudinal axis of said stent against buckling of said stent during insertion of said stent into the urinary tract, including the ureter, such that said stent is always locally essentially parallel with said scope means as said stent is inserted into the urinary tract, whereby said scope means may provide a viewing capability for the insertion of said stent throughout the length of the urinary tract, including the ureter;
(c) placing the first end of the scope means through the lumen of said stent, and;
(d) inserting the first end of the scope and stent through a patient's urethra and bladder and into patient's ureter while observing at least part of the passage through the scope.

23. The method of claim 22 wherein in step (d), the scope and stent are advanced together through the patient's urethra and bladder and into patient's ureter.

24. The method of claim 22 wherein the stent is an open ended stent, wherein the scope is inserted through the lumen of a stent pusher prior to step (c), and wherein in step (d), the scope is first advanced through at least part of the patient's urethra, bladder or ureter, and the stent is then advanced thereover by the stent pusher.

25. The method of claim 22 wherein the scope means is used as a guide wire during the stent insertion.

26. The method of claim 22 wherein a separate guide wire is used during the stent insertion.

27. A method of inserting a ureteral stent comprising:
(a) providing a ureteral stent in the form of a relatively flexible hollow tubular member having first and second stent ends;
(b) providing an elongate flexible scope means having a first scope end for insertion into a patients urinary tract and a second scope end for remaining outside a patient's body, said scope means being a means for providing, outside the patient's body, and image of the region of the patient's body adjacent to the first end of the scope means, said scope means being disposed within the lumen of said stent and supporting said stent along a longitudinal axis of said stent against buckling of said stent during insertion of said stent into the urinary tract, including the ureter, such that said stent is always locally essentially parallel with said scope means as said stent is inserted into the urinary tract, whereby said scope means may provide a viewing capability for the insertion of said stent throughout the length of the urinary tract, including the ureter;
(c) placing the first end of the scope means through the lumen of said stent, and;
(d) inserting the first end of the scope and stent through a patient's urethra and bladder and into patient's ureter while being able to observe at least part of the passage through the scope.

28. The method of claim 27 wherein the scope means is coupled to a video monitor for viewing the image of the region of the patient's body adjacent to the first end of the scope means on the video monitor.

29. The method of claim 28 wherein the scope means is also coupled to a video recorder for recording the image of the region of the patient's body adjacent to the first end of the scope means as viewed on the video monitor.

30. The method of claim 28 wherein the scope means includes an auxiliary opening extending from adjacent said first end thereof along at least most of the length of said scope means, and wherein a laser lithotripsy may be performed through the auxiliary opening during the stent insertion process without withdrawal of the stent or scope.

31. The method of claim 27 wherein the scope means includes an auxiliary opening extending from adjacent said first end thereof along at least most of the length of said scope means, and wherein a laser lithotripsy may be performed through the auxiliary opening during the stent insertion process without withdrawal of the stent or scope.

32. The method of claim 27 wherein the scope means is used as a guide wire during the stent insertion.

33. The method of claim 27 wherein a separate guide wire is used during the stent insertion.

* * * * *